United States Patent [19]

Haitko

[11] Patent Number: 4,594,405

[45] Date of Patent: Jun. 10, 1986

[54] COPPER (I) COMPLEXES USEFUL AS CATALYSTS FOR POLYPHENYLENE OXIDE PREPARATION

[75] Inventor: Deborah A. Haitko, Schenectady, N.Y.

[73] Assignee: General Electric Company, Schenectady, N.Y.

[21] Appl. No.: 572,036

[22] Filed: Jan. 19, 1984

[51] Int. Cl.$^4$ .................. C07F 1/08; C08G 65/38
[52] U.S. Cl. .................. 528/215; 528/212; 528/216; 556/110
[58] Field of Search .............. 260/438.1; 528/212, 528/215; 556/110

[56] References Cited

U.S. PATENT DOCUMENTS

| | | | |
|---|---|---|---|
| 2,686,798 | 8/1954 | Gmitter | 260/438.1 X |
| 2,924,551 | 2/1960 | Harwood et al. | 260/438.1 X |
| 2,924,552 | 2/1960 | Harwood et al. | 260/438.1 X |
| 2,928,856 | 3/1960 | Harwood et al. | 260/438.1 |
| 2,977,279 | 3/1961 | Kosmin | 260/438.1 X |
| 3,038,904 | 6/1962 | Godfrey | 260/438.1 X |
| 3,254,126 | 5/1966 | Griffith et al. | 260/438.1 X |
| 3,914,266 | 10/1975 | Hay | 260/438.1 |

OTHER PUBLICATIONS

Kushioka, *J. Org. Chem.*, 48, 4948-4950 (1983).

*Primary Examiner*—Helen M. S. Sneed
*Attorney, Agent, or Firm*—William H. Pittman; James C. Davis, Jr.; James Magee, Jr.

[57] ABSTRACT

Copper(I)-diamine-chloride complexes are prepared by the reaction of cuprous chloride with a diamine such as N,N'-di-t-butylethylenediamine. Said complexes are reacted with phenoxides such as potassium 2,6-xylenoxide to produce the corresponding copper(I)-diamine-phenoxide complexes, which are useful for the preparation of polyphenylene oxides by oxidative coupling of various phenols such as 2,6-xylenol.

18 Claims, 9 Drawing Figures

FIG. I 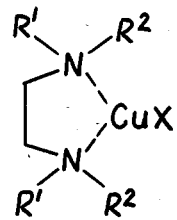
FIG. II 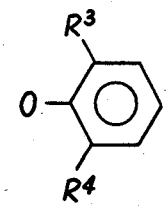
FIG. III 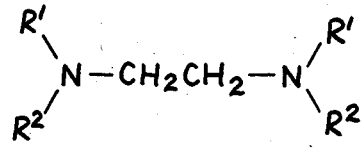
FIG. IV 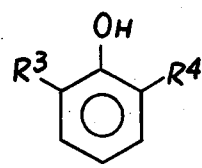
FIG. V 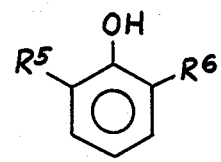

FIG. VI
6.88 6.51 6.31    2.63    1.14
FIG. VII
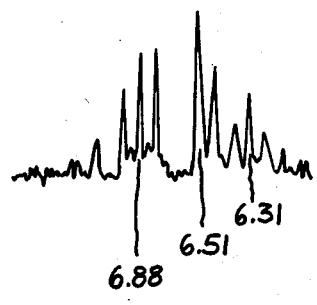
6.88  6.51  6.31

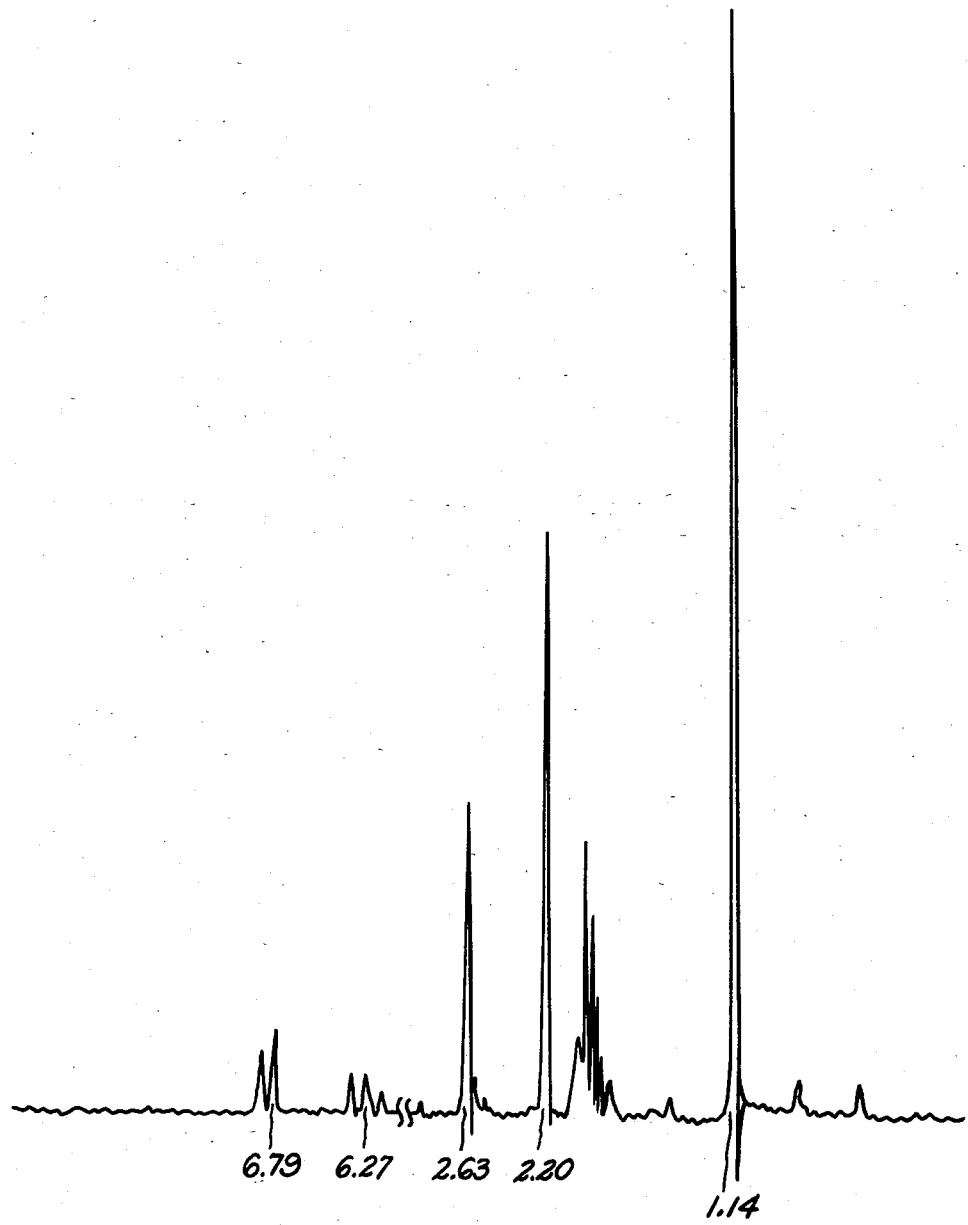
FIG. VIII

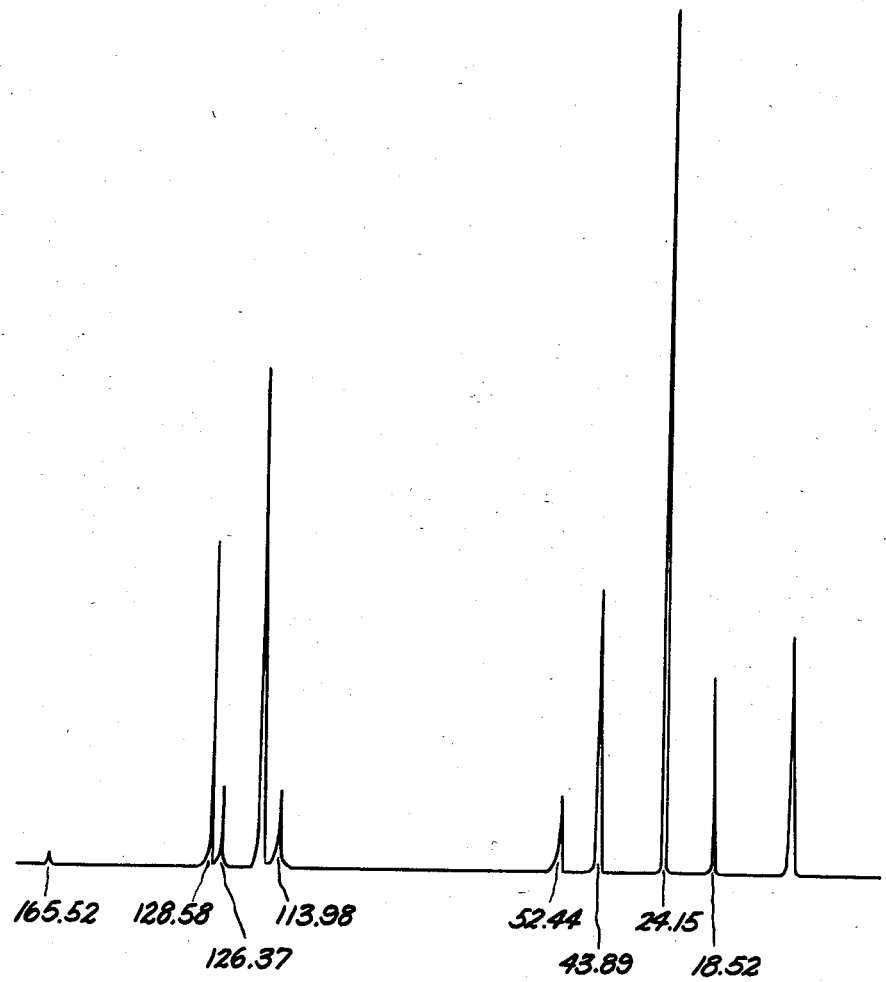
FIG. IX

COPPER (I) COMPLEXES USEFUL AS CATALYSTS FOR POLYPHENYLENE OXIDE PREPARATION

This invention relates to copper(I)-diamine complexes and methods for their preparation and use.

Polyphenylene oxides (also known as polyphenylene ethers) are a well known class of polymeric compositions useful as industrial resins. They are typically prepared by the oxidative coupling of phenols in the presence of copper-halide-amine catalysts. The preparation of catalysts is often effected just before polymerization by blending cuprous or cupric oxide with a halide source, usually a hydrogen halide such as hydrogen chloride or hydrogen bromide, and one or more amines in the presence of an organic solvent. In many such processes a mixture of amines, typically containing a secondary or tertiary alkylene diamine, a secondary monoamine and a tertiary monoamine, is used. Suitable amine mixtures of this type are disclosed in a large number of U.S. patents including the following: U.S. Pat. Nos. 3,306,874; 3,306,875; 3,914,266; 3,988,297; 4,028,341; 4,054,553.

The present invention is based on the discovery of certain diamine-copper(I) phenoxide complexes which can be prepared in substantially pure, crystalline form and which are useful for polyphenylene oxide preparation as a single simple catalyst species.

A principal object of the present invention, therefore, is to provide novel copper(I) complexes and a method for their preparation.

A further object is to provide substantially pure, crystalline copper(I)-diamine-phenoxide complexes useful as catalysts for polyphenylene oxide preparation by oxidative coupling, and novel copper(I)-diamine-chloride precursors therefor.

A further object is to provide a novel and relatively simple method for the preparation of polyphenylene oxides.

Other objects will in part be obvious and will in part appear hereinafter.

In one of its embodiments, the present invention is directed to substantially pure, crystalline copper(I)-diamine complexes having the formula in FIG. I of the drawings. (For the sake of brevity, all references hereinafter to formulas in the drawings will be in the form "formula I", etc., rather than "the formula in FIG. I".) In said formula:

$R^1$ is hydrogen or an alkyl radical and $R^2$ is an alkyl radical, with the provisos that (1) $R^1$ and $R^2$ taken together contain 4–6 carbon atoms and (2) when $R^1$ is hydrogen, $R^2$ is tertiary alkyl;

X is Cl or has formula II; and each of $R^3$ and $R^4$ is independently hydrogen or methyl.

As noted, $R^1$ in formula I may be hydrogen or an alkyl radical and $R^2$ is an alkyl radical. Illustrative alkyl radicals are methyl, ethyl, n-propyl, isopropyl, n-butyl, isobutyl, secondary butyl and tertiary butyl. According to the present invention, the total number of carbon atoms in $R^1$ and $R^2$ taken together is 4–6. Morover, when $R^1$ is hydrogen, $R^2$ must be tertiary alkyl and is preferably tertiary butyl.

The X value may be Cl or may have formula II in which $R^3$ and $R^4$ are each hydrogen or methyl. Most often, both are methyl.

It will be apparent that the copper(I)-diamine complexes of this invention contain moieties derived from a diamine of formula III, and, when X has formula II, from a hydroxyaromatic compound of formula IV. Typical diamines of formula III and N,N,N',N'tetraethylethylenediamine and N,N'-di-t-butylethylenediamine, with the latter being preferred. Suitable hydroxyaromatic compounds include phenol, o-cresol and 2,6-xylenol, with the latter being preferred.

The invention includes copper(I)-diamine-chloride complexes (i.e., those in which X is Cl) irrespective of their purity, although the substantially pure, crystalline copper(I)-diamine-chloride complexes are preferred. Complexes of this structure may be prepared by the reaction of cuprous chloride with a diamine of formula III. Typically, a mole ratio of diamine to cuprous chloride between about 1:1 and about 2:1 is used and the two reagents are brought into contact in the substantial absence of moisture and in a substantially inert atmosphere, in a suitable organic solvent, most often a polar aprotic solvent such as acetonitrile, dimethylformamide, dimethyl sulfoxide or the like. Suitable reaction temperatures are in the range of about 0°–50° C., although generally no heating or cooling is required. The complex often precipitates spontaneously from the organic solvent upon formation; if it does not, it may be precipitated by addition of a non-solvent, by concentration of the solution followed by cooling, or by other conventional methods.

The complexes in which X has formula II are copper-(I)-diamine-phenoxide complexes. They may be prepared by reacting an alkali metal salt of a hydroxyaromatic compound of formula IV with the copper(I)-diamine-chloride complex prepared as described hereinabove. Typically, the copper(I)-diamine-chloride complex and the hydroxyaromatic compound alkali metal salt are dissolved in approximately equimolar proportions in a suitable organic liquid, generally one of those listed hereinabove. This reaction requires scrupulous exclusion of moisture and air, since the complexes are very sensitive to both. On a laboratory scale, the preparation operations are normally conducted under nitrogen dry box conditions. Again, elevated temperatures are seldom if ever required, the reaction proceeding effectively at temperatures within the range of about 0°–50° C. It is frequently preferred to add the hydroxyaromatic compound alkali metal salt gradually to the solution of the copper(I)-diamine-chloride complex. The alkali metal chloride by-product precipitates and is removed from the reaction mixture by filtration or the like, whereupon the substantially pure, crystalline complex of this invention may be isolated by removal of the organic liquid. For this purpose, the hydroxyaromatic compound alkali metal salt is preferably the potassium salt since potassium chloride is quite insoluble in such organic solvents as acetonitrile. Therefore, the present invention includes a method for preparing a substantially pure, crystalline copper(I)-diamine-phenoxide complex which comprises reacting, with the exclusion of moisture and in an inert atmosphere, a sodium or, preferably, potassium salt of a hydroxyaromatic compound of formula IV with a copper(I)diamine-chloride complex in solution in an aprotic polar organic liquid in which sodium or potassium (as appropriate) chloride is insoluble, and removing said chloride and said liquid to yield said crystalline complex. Most often, the salt and complex are employed in substantially equimolar proportions.

The preparation of the copper(I)-diamine complexes of this invention is illustrated by the following examples.

EXAMPLE 1

To a solution of one gram (10 mmol.) of cuprous chloride in 50 ml. of dry, oxygen-free acetonitrile was added 2.15 grams (15 mmol.) of N,N'-di-t-butylethylenediamine which had been distilled from barium oxide and stored under nitrogen. The desired copper(I)-diamine-chloride complex precipitated and was removed by filtration, recrystallized from acetonitrile and dried. The elemental analysis was as follows: carbon, 44.3% (calc. 43.3%); hydrogen, 8.9% (calc. 8.9%); nitrogen, 9.9% (calc. 10.3%); chlorine, 13.9% (calc. 13.1%).

EXAMPLE 2

To a solution of 0.25 gram (0.7 mmol.) of the copper-(I)-diamine-chloride complex of Example 1 in about 50 ml. of acetonitrile was added dropwise, with stirring, a solution in minimal acetonitrile of 0.122 gram (0.9 mmol.) of potassium phenoxide. This addition and all further operations were conducted in a nitrogen dry box, with strict exclusion of oxygen and moisture. Stirring was continued for ten minutes, after which time the precipitated potassium chloride was removed by filtration. Upon vacuum evaporation of the acetonitrile followed by dissolution in minimal acetonitrile and cooling overnight at −40° C., there was obtained in crystalline form the desired copper(I)-(N,N'-t-butylethylenediamine)phenoxide complex.

The molecular structure of the complex is confirmed by its hydrogen nuclear magnetic resonance spectrum in deuterated acetonitrile as solvent, which is illustrated by FIGS. VI and VII. FIG. VII is an expanded version of the portion of FIG. VI in the chemical shift region of 6–7 ppm. The correspondence of the peaks in the spectrum to the various types of hydrogen atoms in the complex is given in TABLE I.

TABLE I

| Chemical shift, ppm. | Hydrogen atom location |
| --- | --- |
| 1.14 | N—t-butyl groups |
| 2.83 | Ethylene group connecting N atoms |
| 6.31 | Phenoxy para position |
| 6.51 | Phenoxy ortho positions |
| 6.88 | Phenoxy meta positions |
| 2.0 (approx.) | Residual H in CD$_3$CN solvent |

EXAMPLE 3

The operations in this example, like those in Example 2, were conducted in a nitrogen dry box with the strict exclusion of oxygen and moisture.

A solution of 2.90 grams (25.9 mmol.) of potassium t-butoxide in minimal tetrahydrofuran was added dropwise to a solution of 3.16 grams (25.9 mmol.) of 2,6-xylenol in dry, oxygen-free tetrahydrofuran. Upon removal of the solvent and by-product t-butyl alcohol in vacuum, there was obtained potassium 2,6-xylenoxide.

A solution of 0.147 gram (0.9 mmol.) of potassium 2,6-xylenoxide in minimal acetonitrile was added dropwise, with stirring, to a solution of 0.25 gram (0.9 mmol.) of the copper(I)-diamine-chloride complex of Example 1 in 50 ml. of acetonitrile. Stirring was continued for 30 minutes, during which time precipitation of a solid was observed. The solid was removed by filtration and was shown by X-ray and chlorine analysis to be potassium chloride. Upon evaporation of the solvent from the filtrate, there was obtained the desired substantially pure, crystalline copper(I)-(N,N-di-t-butylethylenediamine) 2,6-xylenoxide complex. Elemental analysis showed 60.35% carbon (calc. 60.58%), 7.63% nitrogen (calc. 7.85%), 9.07% hydrogen (calc. 9.25%), and 17.70% copper (calc. 17.82%).

FIGS. VIII and IX, respectively, illustrate the hydrogen nuclear magnetic resonance spectrum of the product of Example 3 and the carbon-13 nuclear magnetic resonance spectrum of its carbon-13 counterpart, in deuterated acetonitrile as solvent. The correspondence between the peaks therein and the various types of hydrogen and carbon atoms present in the complex is presented in TABLES II and III, respectively.

TABLE II

| Chemical shift, ppm. | Hydrogen atom location |
| --- | --- |
| 1.14 | N—t-butyl groups |
| 2.20 | Xylenoxy methyl groups |
| 2.63 | Ethylene group connecting N atoms |
| 6.27 | Xylenoxy para position |
| 6.79 | Xylenoxy meta positions |
| 2.0 (approx.) | Residual H in CD$_3$CN solvent |

TABLE III

| Chemical shift, ppm. | Carbon atom location |
| --- | --- |
| 18.52 | Xylenoxy methyl groups |
| 29.15 | N—t-butyl methyl groups |
| 43.89 | Ethylene group connecting N atoms |
| 52.44 | N—t-butyl central atom |
| 113.98 | Xylenoxy ortho position |
| 128.58 | Xylenoxy meta positions |
| 165.52 | Phenolic atom attached to 0 atom |
| 5 (approx.), 120 (approx.) | CD$_3$CN solvent |

EXAMPLE 4

Following the procedure of Example 1, a complex of cuprous chloride with N,N,N',N'-tetraethylethylenediamine was prepared. To a solution of 0.31 gram (1.14 mmol.) of said complex in about 20 ml. of dry, oxygen-free acetonitrile was added dropwise, with stirring, a solution in minimal acetonitrile of 0.183 gram (1.14 mmol.) of potassium 2,6-xylenoxide. When precipitation of potassium chloride was complete, the mixture was filtered and the filtrate was concentrated in vacuum, yielding an off-white oil which may be recrystallized from acetonitrile in accordance with Example 3 to yield the desired crystalline copper(I)-(N,N,N',N'-tetraethylethylenediamine) 2,6-xylenoxide complex.

The copper(I)-diamine-phenoxide complexes of this invention are useful as catalysts for the preparation of polyphenylene oxides by the oxidative coupling of monohydroxyaromatic compounds. Accordingly, another embodiment of the present invention is a method for the preparation of a polyphenylene oxides which comprises oxidatively coupling at least one monohydroxyaromatic compound having formula V, wherein $R^5$ is a lower primary alkyl group and $R^6$ is a lower primary or secondary alkyl group, in the presence of a catalytic amount of at least one copper(I)-diamine-phenoxide complex of this invention. An advantage of said method is that it frequently produces relatively high molecular weight polymer in an unusually short time period.

As used herein, the word "lower" denotes radicals containing up to seven carbon atoms. Examples of lower primary alkyl groups suitable as the $R^5$ moiety are methyl, ethyl, n-propyl, n-butyl, isobutyl, n-amyl, isoamyl, 2-methylbutyl, n-hexyl, 2,3-dimethylbutyl, 2-, 3- or 4-methylpentyl and the corresponding heptyl groups. Examples of lower secondary alkyl groups suitable as the $R^6$ moiety are isopropyl, sec-butyl and 1-ethylpropyl. Preferably, $R^5$ and $R^6$ are straight chain rather than branched. Since the polyphenylene oxides in which $R^5$ and $R^6$ are other than methyl generally have no more desirable properties than those in which they are both methyl, and since 2,6-xylenol is the most readily available and cheapest 2,6-dialkylphenol, its use is preferred.

For the preparation of polyphenylene oxides, oxygen is passed into a mixture of monohydroxyaromatic compound and complex at a temperature typically up to about 40° C. The reaction mixture may also contain a solvent such as toluene, benzene or acetonitrile; the latter is preferred because of the solubility therein of the copper(I)diamine-phenoxide complexes of this invention. Oxygen passage is typically at a rate of about 0.8-1.2 SCFH, and the amount of oxygen is generally about 0.5-1 mole per mole of monohydroxyaromatic compound. If desired, the oxygen can be diluted with inert gases or air can be used, but the use of pure oxygen is preferred. The molar ratio of monohydroxyaromatic compound to copper in the complex may be about 100-1500:1 and is preferably about 250-1000:1.

Upon passage of oxygen through the above-described mixture, an exothermic reaction normally takes place. It is preferred to maintain the maximum temperature no higher than about 45° C., which maximizes the molecular weight of the polyphenylene oxide produced.

In order to produce a uniform polymer, it is generally preferred to use a single monohydroxyaromatic compound whose structure corresponds to that of the phenoxide groups in the complex. For example, 2,6-xylenol polymerization may be effected using copper(I)-(N,N'-di-t-butylethylenediamine) 2,6-xylenoxide. It is, however, also within the scope of the invention to employ a mixture of monohydroxyaromatic compounds or to use a catalyst having a different phenoxide group from that present in the monohydroxyaromatic compound, whereupon a mixed polymer may be obtained.

When the polymerization reaction is complete, it may be desirable to remove traces of copper entrained therein from the catalyst. Such removal may be conveniently effected by treating with a sequestrant such as ethylenediaminetetraacetic acid or a salt thereof. Depending on the solvent used, the polymer may precipitate as it is formed or it may remain in solution; in the latter instance, it may be recovered by conventional methods such as precipitation by addition of a non-solvent.

The polyphenylene oxide preparation method of this invention is illustrated by the following examples. All parts and percentages are by weight.

EXAMPLE 5

An approximately 25% solution of 2,6-xylenol in acetonitrile was purged with oxygen and an acetonitrile solution of copper(I)-(N,N'-di-t-butylethylenediamine) 2,6-xylenoxide was added in an amount to afford a molar ratio of xylenol to copper of 300:1. Oxygen passage was continued for 60 minutes, resulting in an exothermic reaction during which a maximum temperature of 43° C. was attained. The desired polyphenylene oxide precipitated from the reaction mixture as it was formed; it was dissolved in chloroform, extracted with a 10% aqueous solution of trisodium ethylenediaminetetraacetate, precipitated by the addition of methanol, filtered and dried. The weight average molecular weight, determined by gel permiation chromatography, was 27,000.

EXAMPLE 6

The procedure of Example 5 was repeated, except that the molar ratio of 2,6-xylenol to copper was 900:1, the total reaction time was 10 minutes and the trisodium ethylenediaminetetraacetate extraction step was omitted. The resulting polymer had a molecular weight of about 15,800.

What is claimed is:

1. A substantially pure, crystalline copper(I)-diamine complex having the formula

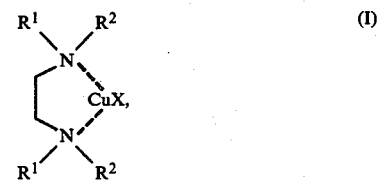

wherein:

$R^1$ is hydrogen or an alkyl radical and $R^2$ is an alkyl radical, with the provisos that (1) $R^1$ and $R^2$ taken together contain 4-6 carbon atoms and (2) when $R^1$ is hydrogen, $R^2$ is tertiary alkyl;

X is Cl or

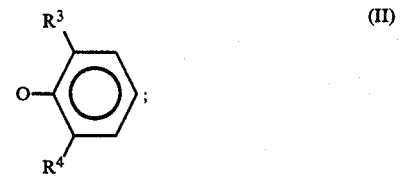

and each of $R^3$ and $R^4$ is independently hydrogen or methyl.

2. A complex according to claim 1 wherein X has formula II.

3. A complex according to claim 2 wherein $R^1$ is hydrogen and $R^2$ is tertiary alkyl.

4. A complex according to claim 3 wherein $R^2$ is tertiary butyl and each of $R^3$ and $R^4$ is hydrogen.

5. A complex according to claim 3 wherein each of $R^3$ and $R^4$ is methyl.

6. A complex according to claim 5 wherein $R^2$ is tertiary butyl.

7. A copper(I)-diamine-chloride complex having the formula

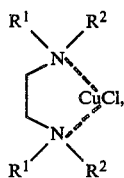

wherein $R^1$ is hydrogen or an alkyl radical and $R^2$ is an alkyl radical, with the provisos that (1) $R^1$ and $R^2$ taken together contain 4–6 carbon atoms and (2) when $R^1$ is hydrogen, $R^2$ is tertiary alkyl.

8. A complex according to claim 7 wherein $R^1$ is hydrogen and $R^2$ is tertiary alkyl.

9. A complex according to claim 8 wherein $R^2$ is tertiary butyl.

10. A method for preparing a complex according to claim 2 which comprises reacting at a temperature within the range of about 0°–50° C., with the exclusion of moisture and in an inert atmosphere, a sodium or potassium salt of a hydroxyaromatic compound having the formula

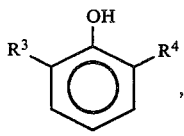 (IV)

wherein each of $R^3$ and $R^4$ is independently hydrogen or methyl, with a copper(I)-diamine-chloride complex having the formula

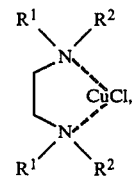

in solution in an aprotic polar organic liquid in which sodium or potassium chloride is insoluble, and removing said chloride and said liquid to yield said crystalline complex.

11. A method according to claim 10 wherein the salt of the hydroxyaromatic compound is a potassium salt.

12. A method according to claim 11 wherein $R^1$ is hydrogen and $R^2$ is tertiary butyl.

13. A method according to claim 12 wherein each of $R^3$ and $R^4$ is hydrogen.

14. A method according to claim 12 wherein each of $R^3$ and $R^4$ is methyl.

15. A method for the preparation of a polyphenylene oxide which comprises oxidatively coupling at least one monohydroxyaromatic compound having the formula $$R^5 \text{—} \underset{\underset{\text{OH}}{|}}{\text{C}_6\text{H}_3} \text{—} R^6 \quad (V)$$

wherein $R^5$ is a lower primary alkyl group and $R^6$ is a lower primary or secondary alkyl group, in the presence of a catalytic amount of at least one complex according to claim 2.

16. A method according to claim 15 wherein each of $R^5$ and $R^6$ is methyl.

17. A method according to claim 16 wherein $R^1$ is hydrogen and $R^2$ is tertiary butyl.

18. A method according to claim 17 wherein each of $R^3$ and $R^4$ is methyl.

* * * * *